United States Patent [19]

Shoesmith, deceased et al.

[11] Patent Number: Plant 7,682

[45] Date of Patent: Oct. 22, 1991

[54] CHRYSANTHEMUM PLANT NAMED PENSACOLA

[75] Inventors: Leonard H. Shoesmith, deceased, late of Woking, England, by May Victoria Shoesmith, executrix; May V. Shoesmith, Woking, both of England; Peter S. Hesse, Nipoma, Calif.

[73] Assignee: Yoder Brothers, Inc., Barberton, Ohio

[21] Appl. No.: 562,379

[22] Filed: Aug. 3, 1990

[51] Int. Cl.[5] ..... A01H 5/00

[52] U.S. Cl. ..... Plt./74

[58] Field of Search ..... Plt./74, 74.1, 82.2

*Primary Examiner*—Howard J. Locker

*Attorney, Agent, or Firm*—Foley & Lardner

[57] ABSTRACT

A Chrysanthemum plant named Pensacola particularly characterized by its flat capitulum form; daisy capitulum type; yellow ray floret color; diameter across face of capitulum of 95 to 105 mm. when fully opened; flowering response ranging from 60 to 65 days after start of short days; peduncle length of first lateral ranging from 5 to 13 cm., of the fourth lateral from 13 to 20 cm. on open, terminal sprays; plant height when grown as a single stem cut mum in Parrish, Fla., with 19 to 25 long days prior to start of short days is 130 to 135 cm.

3 Drawing Sheets

The present invention comprises a new and distinct cultivar of Chrysanthemum, botanically known as *Dendranthema grandiflora*, and referred to by the cultivar name Pensacola.

Pensacola, identified as SP82-7865-YS, was originated from a cross made by Leonard H. Shoesmith and May Victoria Shoesmith in a controlled breeding program in Westfield-Woking, England, in 1981.

Both the female and the male parents of Pensacola were unknown seedlings from Shoesmith breeding lines.

Pensacola was discovered and selected as one flowering plant within the progeny of the stated cross by Peter S. Hesse in November 1982, in a controlled environment in Bradenton, Fla.

The first act of asexual reproduction of Pensacola was accomplished when vegetative cuttings were taken from the initial selection in January 1983 in a controlled environment in Bradenton, Fla., by technicians working under the supervision of Peter S. Hesse.

Horticultural examination of controlled flowerings of successive plantings has shown that the unique combination of characteristics as herein disclosed for Pensacola are firmly fixed and are retained through successive generations of asexual reproduction.

Pensacola has not been observed under all possible environmental conditions. The phenotype may vary significantly with variations in environment such as temperature, light intensity and daylength. For example, plant height will increase with an increased number of long days after planting prior to start of short days. Under low night temperatures (10 degrees Celsius and lower) flowering can be expected to be delayed. Under high temperatures (25 degrees Celsius night and 35 degrees Celsius day) flowering can be expected to be delayed and also be more uneven than under normal temperatures. Normal temperatures can be described as 15 degrees Celsius minimum night and 25 degrees Celsius maximum day.

The following observations, measurements and comparisons describe plants grown at various locations in the United States, including Parrish and Palmetto, Fla., under greenhouse conditions which approximate those generally used in commercial greenhouse practice.

The following traits have been repeatedly observed and are determined to be basic characteristics of Pensacola, which, in combination, distinguish this Chrysanthemum as a new and distinct cultivar:

1. Flat capitulum form.
2. Daisy capitulum type.
3. Yellow ray floret color.
4. Diameter across face of capitulum of 95 to 105 mm when fully opened.
5. Flowering response ranges from 60 to 65 days after start of short days when grown in the United States.
6. Peduncle length of the first lateral at flowering after removing the apical bud without growth regulator applications is 5 to 13 cm when grown in the United States. Peduncle length of the fourth lateral at flowering is 13 to 20 cm. on open, terminal sprays.
7. Plant height when grown as a single stem cut mum in Parrish, Fla., with 19 to 25 long days prior to start of short days is 130 to 135 cm.

The accompanying photographic drawings show typical inflorescence and leaf characteristics of Pensacola, with the colors being as nearly true as possible with illustrations of this type.

Sheet 1 is a color photograph of Pensacola grown as a single stem cut spray mum.

Sheet 2 is a black and white photograph of three views of the inflorescence of Pensacola.

Sheet 3 is a black and white photograph showing the upper and under sides of the leaves of Pensacola at three stages of development (mature, intermediate and immature).

Of the cultivars known to the inventors, the most similar in comparison to Pensacola is the cultivar identified as Florida Marble, a yellow flat daisy cut spray mum, disclosed in U.S. Plant Pat. No. 3,288. Reference is made to attached Chart A, which compares certain characteristics of Pensacola to the same characteristics of Florida Marble.

Similar traits are capitulum form and type. Although both Pensacola and Florida Marble are generally described and classed as yellow, the ray floret color of Pensacola is a much deeper and more intense yellow than the ray floret color of Florida Marble. The spray formation of Pensacola is always terminal, while Florida Marble often exhibits a compound spray formation. Pensacola has shorter peduncles and a much larger diameter of capitulum than Florida Marble. The plant height and flowering response of both cultivars is comparable. In addition, Florida Marble often exhibits bracts in the center of the disc. Pensacola does not exhibit this trait.

In the following description color references are made to The Royal Horticultural Society Colour Chart. The color values were determined on plant material grown in Salinas, Calif., on Dec. 13, 1989.

Classification:

*Botanical.*—*Dendranthema grandiflora* cv Pensacola.

*Commercial.*—Daisy cut spray mum.

INFLORESCENCE

A. Capitulum:

*Form,*—flat.

*Type.*—Daisy.

*Diameter across face.*—95 to 105 mm. when fully opened.

B. Corolla of ray florets:

*Color (general tonality from a distance of three meters).*—Yellow.

*Color (upper surface).*—7A to 7B.

*Color (under surface).*—7C to 7D.

*Shape.*—Straight flat, pointed. Immature flowers show longitudinal petal roll (see photograph sheet 1).

C. Corolla of disc florets:

*Color (mature).*—Closest to 14A, with center of disc overlaid with 144B.

*Color (immature).*—Closest to 144A.

D. Reproductive organs:

*Androecium.*—Present on disc florets only; moderate pollen.

*Gynoecium.*—Present on both ray and disc florets.

PLANT

A. General appearance:

*Height.*—Plant height is 130 to 135 cm. when grown as a single stem cut mum in Parrish, Fla., with 19 to 25 long days prior to start of short days.

B. Foliage:

*Color (upper surface).*—147A.

*Color (under surface).*—147B.

*Shape.*—See photograph.

CHART A

COMPARISON OF PENSACOLA AND FLORIDA MARBLE

| CHARACTERISTIC | PENSACOLA | FLORIDA MARBLE |
|---|---|---|
| Ray floret color | Yellow | Yellow |
| Capitulum form | Flat | Flat |
| Capitulum type | Daisy | Daisy |
| Spray formation | Terminal | Terminal to compound |
| Penduncle length | | |
| 1st lateral | 5 to 13 cm. | 15 to 23 cm. |
| 4th lateral | 13 to 20 cm. | 20 to 25 cm. |
| Diameter across face of capitulum | 95 to 105 mm. | 75 to 90 mm. |
| Plant height 19-25 long days, Parrish | 130 to 135 cm. | 119 to 140 cm. |
| Flowering response period in United States at Parrish and Palmetto, Florida | 60 to 65 days | 51 to 68 days |

COMPARISONS MADE OF PLANTS GROWN AS SINGLE STEM SPRAY CUT MUMS IN VARIOUS LOCATIONS IN THE UNITED STATES

I claim:

1. A new and distinct Chrysanthemum plant named Pensacola, as described and illustrated.

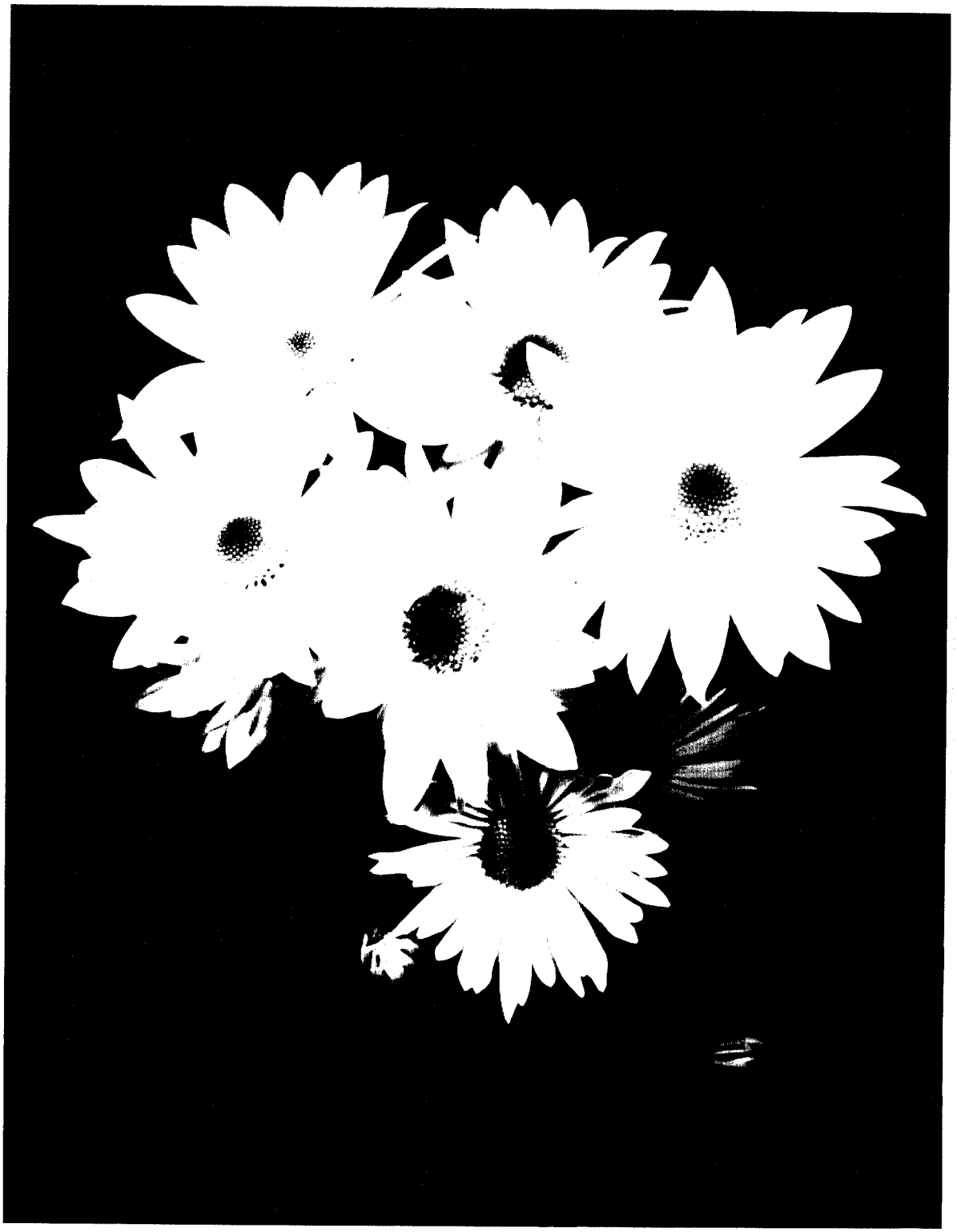

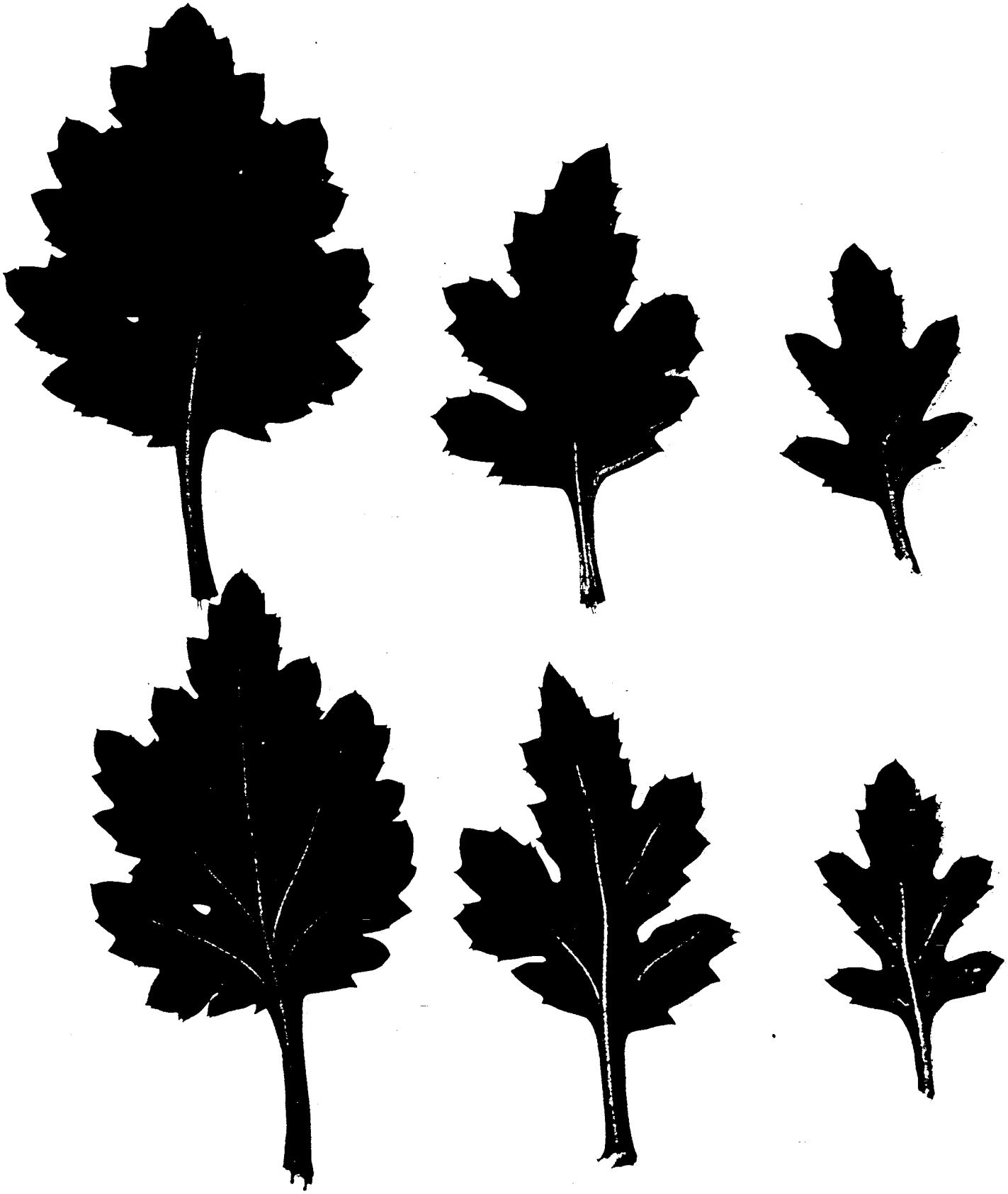

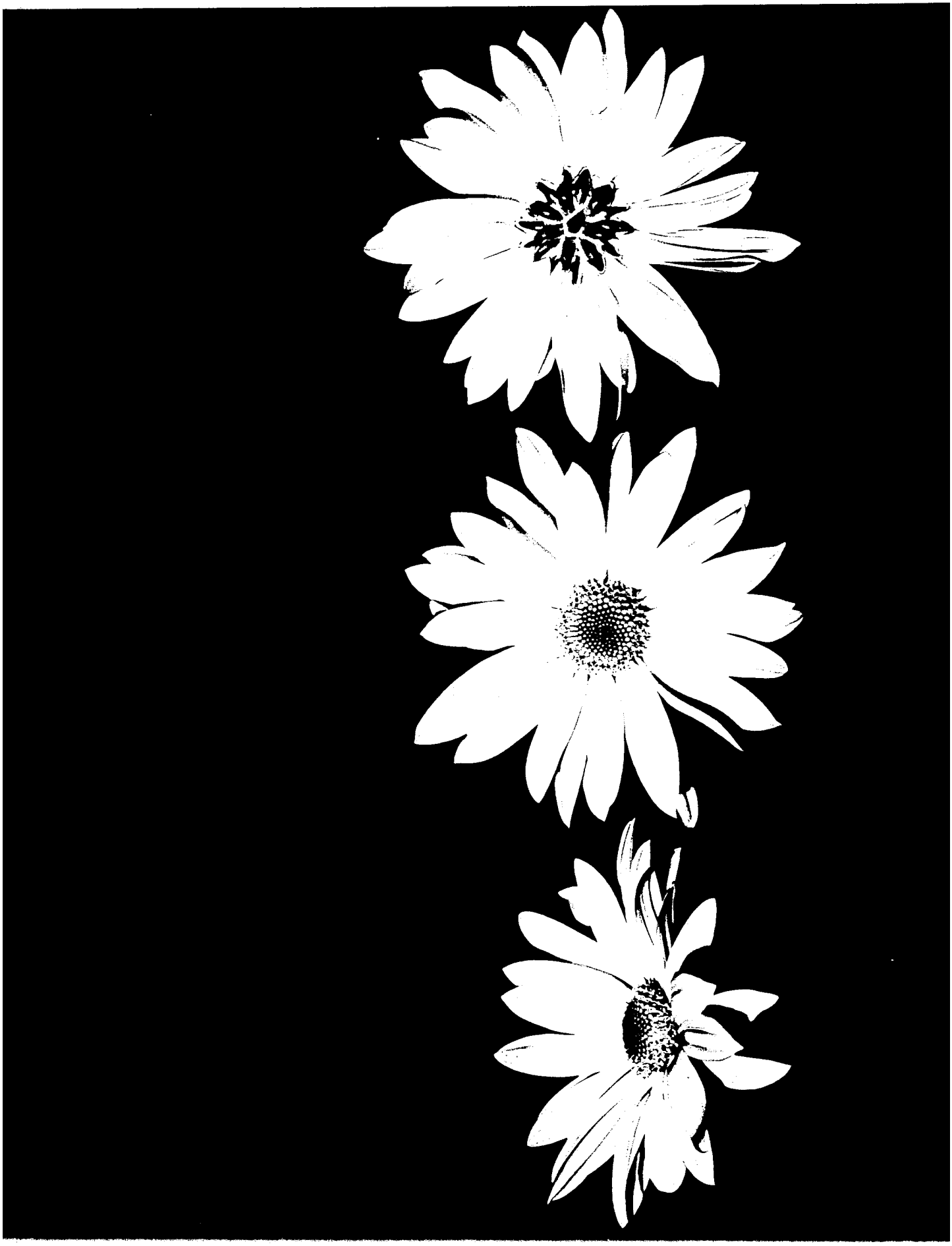

* * * * *